United States Patent [19]
Honeywell et al.

[11] Patent Number: 5,305,754
[45] Date of Patent: Apr. 26, 1994

[54] HEAD IMMOBILIZATION DEVICE

[76] Inventors: Valerie S. Honeywell; Paul J. Honeywell, both of 37502 NE. Olstedt Rd., La Center, Wash. 98629

[21] Appl. No.: 808,664

[22] Filed: Dec. 17, 1991

[51] Int. Cl.[5] .................... A61B 19/00; A61F 5/37
[52] U.S. Cl. .................... 128/869; 128/870; 5/637; 5/626; 5/924; 602/17
[58] Field of Search ............. 128/857, 869, 870, 858, 128/864, 866; 602/17, 18; 5/624, 625, 626, 628, 636, 637, 640, 924

[56] References Cited

U.S. PATENT DOCUMENTS

| | | | |
|---|---|---|---|
| 2,587,196 | 2/1952 | Morecroft | 5/640 |
| 2,765,480 | 10/1956 | Mueller | 5/640 |
| 3,481,593 | 2/1969 | Allen et al. | 5/924 X |
| 3,897,777 | 8/1975 | Morrison | 5/637 X |
| 4,031,578 | 6/1977 | Sweeney et al. | 5/636 X |
| 4,400,820 | 8/1983 | O'Dell et al. | 128/869 X |
| 4,550,458 | 11/1985 | Fiore | 5/637 |
| 4,571,757 | 2/1986 | Zolecki | 128/869 X |
| 4,928,711 | 5/1990 | Williams | 128/870 X |
| 4,964,418 | 10/1990 | Wilson | 128/857 |

OTHER PUBLICATIONS

HeadBead II by California Medical Products, Inc., Long Beach, California.

*Primary Examiner*—Robert A. Hafer
*Assistant Examiner*—Brian E. Hanlon
*Attorney, Agent, or Firm*—Klarquist, Sparkman, Campbell, Leigh & Whinston

[57] ABSTRACT

A head immobilization device for an accident patient and a manufacturing blank of sheet material, such as cardboard, for making such a device are described. The manufacturing blank is H-shaped and provided with fold lines. The blank is folded to form the head immobilization device with a pair of triangular cylinders which extend longitudinally upward from the top surface of a head support center section on opposite sides of such section to prevent lateral movement of the head. The head immobilization device is provided with adhesive tape on the bottom surface of the center section to attach such device to a flat support such as a back-board. Ear hole slots are provided in the inner sides of the triangular cylinders to enable examination of the ears. The sides of the triangular cylinders are releasably fastened by hook and loop fasteners.

9 Claims, 2 Drawing Sheets

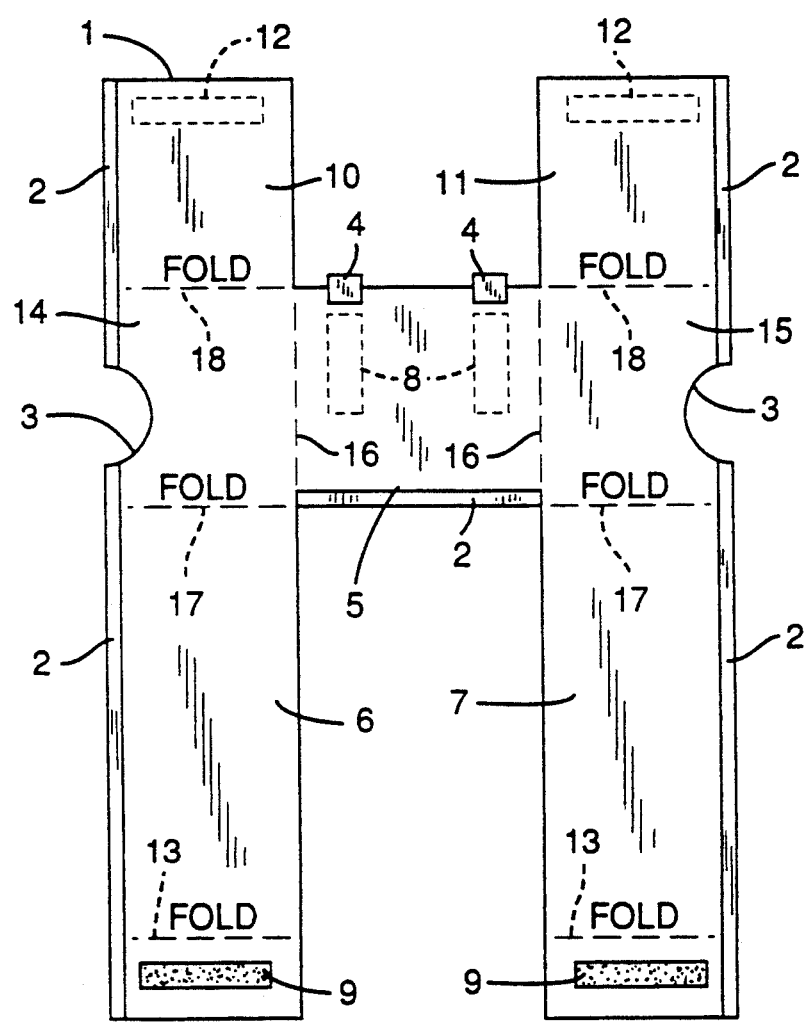

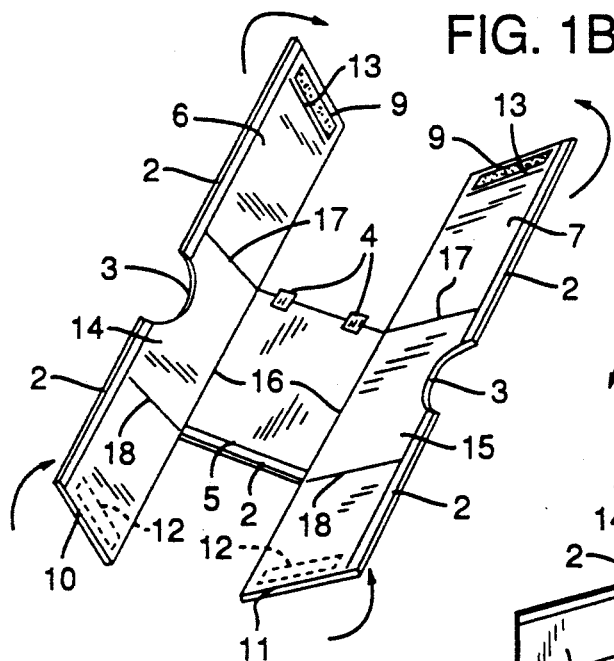
FIG. 1B (1)
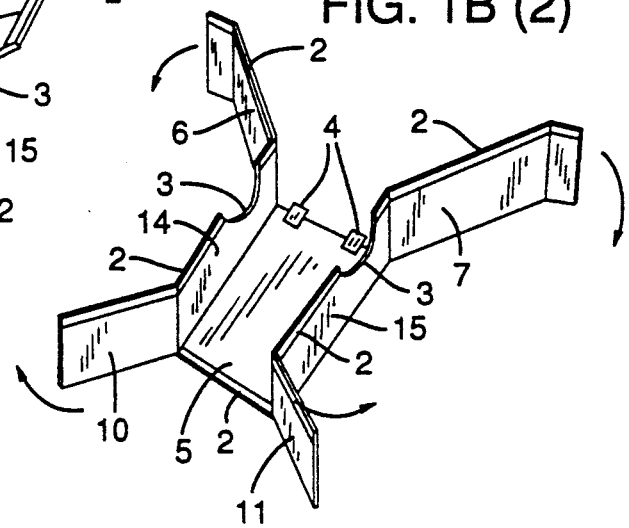
FIG. 1B (2)
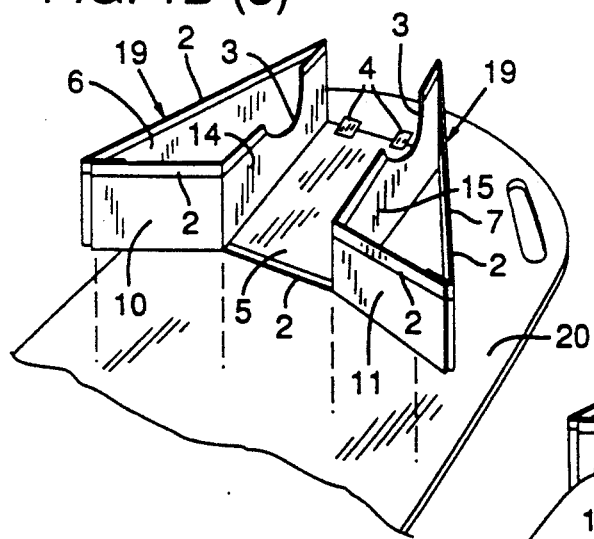
FIG. 1B (3)
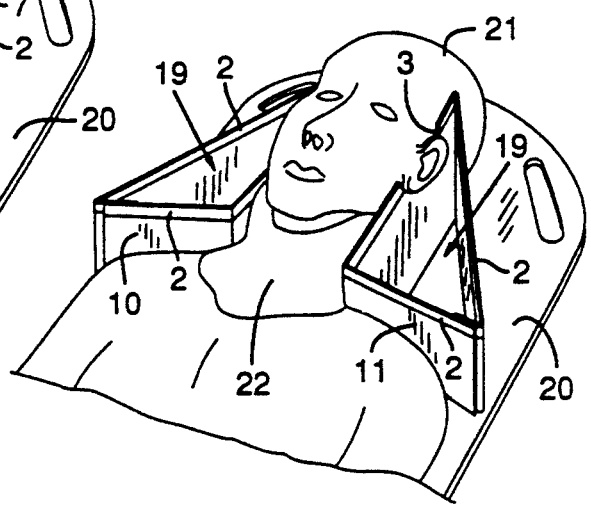
FIG. 1B (4)

HEAD IMMOBILIZATION DEVICE

The present invention relates to a head immobilization device, hereafter referred to as Headlock TM, and a manufacturing blank for making such device.

Headlock is a head immobilization device for emergency medical rescuers and other medical personnel to use on patients involved in the event of a suspected cervical spine injury. Headlock functions as a better means of protection against further harm to a patient's cervical spine. This invention is used in coordination with other standard medical equipment such as a backboard and a cervical collar to control a patients cervical spine.

BACKGROUND OF THE INVENTION

Head restraints are products that are intended to assist in limiting the movement of a patient's head and neck after an accident in which said patient's spine and/or head has been or may be injured. Head restraints are both disposable or re-usable, depending on each independent product.

Disadvantages of a nondisposable head restraint are high cost and frequent replacement due to loss or damage. The disadvantages of the disposable cardboard head restraint used at this time are inefficiency of adequate head immobilization. The tape for taping the head restraint to a back board, that also comes with other cardboard head restraints, is difficult to keep from becoming twisted and stuck to gloved hands during application to the patient. Application of other head restraints has been obviously confusing to many Emergency Medical Technicians, thus wasting valued time to patient's welfare.

The Headlock head restraint of the present invention is superior in immobilizing the patient's head compared to other cardboard restraints. Common sense methods in application make the Headlock a more desirable choice for restraining a patient's head and spine (cervical region). The design of the H-shape manufacturing blank sheet enables it to be folded to form triangular cylinders extending upward on either side of the patient's head which considerably reduces lateral head movement. The simplicity of being able to examine ears, with the incorporation of ear slots on the sides of the triangular cylinders is a great benefit. Simplicity with superior immobilization makes the Headlock much more desirable.

DESCRIPTION OF THE DRAWINGS

The drawing in FIG. 1-A shows the H-shape of the manufacturing blank sheet material from which the Headlock is formed.

FIG. 1-B shows by steps (1), (2), (3) and (4) how Headlock is folded, put together, and used on a patient.

DETAILED DESCRIPTION

Material used for Headlock include: H-shaped rigid sheet material 1, such as two hundred pound weather resistant cardboard, one side white and the other side brown, with head support sheet center section 5 and side strips 6 and 7. One inch wide tape 2 on outer sides wrapped around edge with 3m brand. Ear slots 3 sealed with RTV silicone rubber with 3m brand. Brown wax paper 4 one inch wide slipped through one inch slots on head area (cross section) used to cover two sided tape 8. This two sided tape is to be exposed when Headlock is used on a flat surface, such as a back board, for application to a patient. To produce a Headlock head immobilization device a 24"×14½" manufacturing blank of rigid sheet material, such as weather resistant 200# cardboard, is required. This cardboard blank is white on one side and brown on the reverse side. Headlock blank is cut into the shape of an H including a head support sheet center section 5 upon which lies a head 21 of the patient. This shape does show the center cross-section of the H closer to one end. This head support section 5 is 7" long for small people, 7½" long for the adult, and 8" long for the large size people. This head support section of the H is 5½" wide for the small person, 6" wide for the adult, and 6½" wide for the large size people. On the backside of this center section 5 are two strips of foam tape 8 approximately 2" long by 1" wide. This foam tape 8 is positioned 1" down from the upper edge of the center section and runs parallel to the side flaps of this H-shape. On this foam tape is 1" two-sided adhesive with wax paper protection. This adhesive covers the foam tape completely, the wax paper covers the adhesive completely and then continues on approximately 3" long to make a tail 4. This tail 4 of wax paper is slid through 1¼" slots located approximately five eights of an inch down from the top edge on the center section 5. The purpose for these wax paper tails 4 are for easy application of the Headlock to desired flat surfaces such as a wooden back-board 20. Once these wax paper tails are pulled free, the two-sided adhesive tape 8 is exposed for use.

Connected to the head support section 5 of the Headlock are a pair of 4" wide side strips that are the sides of the H-shape. These vertical sides are exactly the same length, each being 24" long. These side strips include first end portions 6 and 7 which run from end to center section 10" for small people, and 11½" for both the adult and the large size. This first end strip 6 is equal in length exactly to the first strip 7 on opposite side of the H-shape. At the end of this first end strip is a fastener device 9, such as a 1" wide by 2" long piece of "hook and loop" Velcro TM fastener, being only the hook material located at this section. This hook piece 9 is secured by its own adhesive to the cardboard end strips 6 and 7 horizontally approximately 1" from edge and centered between sides equally. This end of strip is scored at fold line 13 for folding two and five eights of an inch up. At the other end of the H are a pair of second end strips 10 and 11 that are 5" long on the adult and large sizes and 4½" long on the small size extending from the center section 5. These two end strips 10 and 11 are exactly the same length. At the ends of the second end strips are the two loop pieces 12 of the hook and loop material. The loop material here is approximately 1" from the edge and runs horizontally 2" long. These loop pieces 12 are on the back (brown) side of the cardboard. Weather resistant tape 2 is wrapped around the outer edges of the side strips of the H-shaped sheet 1 along its full length of 24", with exception of ear holes 3 incorporated on the outer edge of the middle portions 14 and 15 of the side strips. These ear slots 3 are moon shaped and are located at the outer edge of the middle side strips 14, 15. Silicone is used to seal the edge of the ear slots from wet weather and other fluids.

To use the Headlock, fold the middle side strips 14 and 15 of the H up where score lines 16 are present at a location where the middle side strips meet center section 5. Fold the scored ends on the first end long strips 6 and 7 with the hook material 9 forcefully over along fold lines 16. Then bend the end strips 6 and 7 out along fold lines 17 and the second end strips 10 and 11 out along fold lines 18 and continue to bend the long side strips 6 and 7 to meet the short side strips 10 and 11 with the loop material 12. Once the hook material 9 and loop material 12 meet, the side of this H-shape will have formed a triangular cylinder. This results in a pair of triangular cylinders 19 on opposite sides of the center section 5. The triangular cylinders 19 will stand 4" high on both sides of center section 5 and extend longitudinally upward and substantially perpendicular to the top of such center section. The triangular cylinders are spaced apart by a spacing fixed distance substantially the same as of the maximum width of the patient's head for providing lateral support to prevent lateral movement of the head and thereby will act as security for the patient's head. The wax paper tails 4 should be pulled when the Headlock is ready for securing to a flat, firm surface, such as a wooden back-board 20, upon which the patient lies as shown in FIG. 1-B(4). Thus, the patient's head 21 lies on the center section 5 of the Headlock and is immobilized by tape extending over the forehead and/or chin of the patient to the back-board in a conventional manner (not shown). In addition, a cervical collar 22 may be fastened to the neck of the patient beneath the chin to further immobilize the head.

We claim:

1. A head immobilization device, comprising:
   head support sheet having top and bottom surfaces supporting the head of a patient; and
   a pair of lateral support members for preventing lateral movement of the head, each lateral support member being a triangular cylinder of sheet material having three sides and a triangular cross-section, said cross-section being substantially parallel to the head support sheet with said sides extending in height at an angle away from said support sheet, and said cylinder extending longitudinally upward from the top surface of the head support sheet to provide a pair of triangular cylinders, each cylinder having an inner side and the inner sides of said pair of cylinders being spaced apart by a fixed spacing distance substantially the same as the maximum width of the head.

2. A device in accordance with claim 1 in which the triangular cylinders each have a bottom side which is adapted to engage the shoulder of the patient.

3. A device in accordance with claim 1 in which the triangular cylinders each have an ear hole in an inner side of said cylinder to accommodate the ears of the patient.

4. A device in accordance with claim 1 in which the head support sheet is provided with attachment means for attaching said support sheet to a flat support member.

5. A device in accordance with claim 4 in which the attachment means is an adhesive attachment means.

6. A device in accordance with claim 1 in which the triangular cylinders are integral with the head support sheet and extend longitudinally substantially perpendicular to the top surface of said support sheet.

7. A device in accordance with claim 6 in which said cylinders are formed by folding two side strips of sheet material and the opposite ends of each side strip are fastened together by a releasable fastening means.

8. A device in accordance with claim 7 in which the fastening means is a hook and loop fastening means.

9. A device in accordance with claim 1 in which the triangular cylinders have cross-sections which are right triangles.

* * * * *